(12) United States Patent
Yang et al.

(10) Patent No.: US 8,470,363 B2
(45) Date of Patent: Jun. 25, 2013

(54) ANTIHYPERTENSIVE PHARMACEUTICAL COMPOSITION

(75) Inventors: Yan ling Yang, Shanghai (CN); Chuan xiao Xue, Shanghai (CN); Xi tian Zhang, Shanghai (CN); Huan Li, Shanghai (CN); Sen tao Song, Shanghai (CN)

(73) Assignee: Shihuida Pharmaceuticals Group (JILIN) Ltd. (CN)

( * ) Notice: Subject to any disclaimer, the term of this patent is extended or adjusted under 35 U.S.C. 154(b) by 99 days.

(21) Appl. No.: 13/123,609

(22) PCT Filed: Jun. 17, 2010

(86) PCT No.: PCT/CN2010/073998
§ 371 (c)(1),
(2), (4) Date: Apr. 11, 2011

(87) PCT Pub. No.: WO2011/097857
PCT Pub. Date: Aug. 18, 2011

(65) Prior Publication Data
US 2011/0263660 A1   Oct. 27, 2011

(51) Int. Cl.
*A61K 9/44* (2006.01)
*A61K 9/48* (2006.01)

(52) U.S. Cl.
USPC .......................................................... 424/451

(58) Field of Classification Search
USPC .......................................................... 424/451
See application file for complete search history.

(56) References Cited

U.S. PATENT DOCUMENTS

| 4,755,386 A * | 7/1988 | Hsiao et al. ............... 424/435 |
| 6,291,490 B1 * | 9/2001 | Young ............................ 514/356 |
| 2001/0004640 A1 * | 6/2001 | Inada et al. .................. 514/393 |
| 2005/0202086 A1 * | 9/2005 | Jureczek ...................... 424/468 |
| 2007/0237815 A1 * | 10/2007 | Solomon et al. ............. 424/451 |

\* cited by examiner

*Primary Examiner* — Shirley V Gembeh
(74) *Attorney, Agent, or Firm* — Bacon & Thomas, PLLC

(57) ABSTRACT

An antihypertensive pharmaceutical composition is provided, which contains levamlodipine or a pharmaceutically acceptable salt thereof, and indapamide. In the present invention, levamlodipine and indapamide are administrated in combination for treating hypertension, a good synergistic antihypertensive effect is achieved, and the edema side effect due to sodium and water retention caused when levamlodipine is administrated alone and the side effect of glucose metabolism interference caused when indapamide is administrated alone are mitigated.

19 Claims, No Drawings

ANTIHYPERTENSIVE PHARMACEUTICAL COMPOSITION

BACKGROUND OF THE INVENTION

1. Field of Invention

The present invention relates to the pharmaceutical field, and more particularly to an antihypertensive pharmaceutical composition.

2. Related Art

In recent years, with the continuous improvement of living standards and the changes in the dietary structure of Chinese people, the increase of life stress, and the increase of the elderly population, the incidence of hypertension is gradually increased, and at the same time hypertension causes lesions to heart, brain, kidneys, and other organs, is closely related to sugar and lipid metabolism disorders and diabetes, significantly reduces the quality of life of patients, and even threatens the lives of patients in serious cases. A large number of international authoritative clinical studies on hypertension suggest that increased efforts for depressing the blood pressure, and active and sustained depressing of the blood pressure in the hypertension patients below 130/85 mmHg (optimally below 120/80 mmHg) may effectively mitigate lesions of target organs such as heart, brain, and kidneys caused by hypertension, reduce or delay complications such as stroke, coronary heart disease, angina, myocardial infarction, renal failure, atherosclerosis, and aneurysm, reduce the incidence of the cardiovascular events, the mortality, and the morbidity, improve the life quality of the patients, and prolong the life of the patients. According to the global mortality statistics of various diseases of the World Health Organization (WHO), the cardiovascular disease deaths represented by hypertension accounts for 36% of the total number of deaths; therefore, improving people's awareness on hypertension is of great importance for early-stage prevention and timely treatment.

2008 Consensus of Chinese Experts in Diagnosis and Treatment of Elderly Patients with Hypertension indicates that, treatment through combined administration utilizes multiple different mechanisms for depressing blood pressure, good antihypertensive effect is achieved, adverse reactions are fewer, and thus being more beneficial for protection of target organs. Numerous studies show that, in order to achieve the purpose of positive and intensive blood pressure depression, 70-100% of the patients need to be administrated with two or more antihypertensive drugs in combination. The combined administration can not only significantly improve the antihypertensive effect due to the additive or synergistic effects of the drugs, but also can reduce the side effects of the drugs, and thus the safety and the patient compliance are improved. A lot of literatures suggest that, due to reasonable combination of two antihypertensive drugs, the adverse effects of the two combined ingredients when administrated separately may also be counteracted. Therefore, when a conventional dose of a single medicine cannot achieve the desired standard effect, it is recommended to adopt a combined administration regimen including compound preparations to treat hypertension patients.

Levamlodipine is an optical pure medicine that is firstly chirally resolved in China, an anti hypertensive medicine that is firstly chirally resolved in the world, and a long-term basic dihydropyridine calcium antagonists, and may be prepared through many methods, see references CN00102701.8 and CN03821593.4. Levamlodipine functions through a site (N site) attached to dihydropyridine on a cell and blocks calcium ions from entering the cardiac and vascular smooth muscle cells in a transmembrane manner, so as to relax the smooth muscle, decrease the vascular resistance, and lower the blood pressure. Presently, clinical trial evidences indicate that, a therapeutic dose of levamlodipine has very slight or no influence on cardiac contractility and atrioventricular conduction, and levamlodipine is a medicine with the minimal effect on sympathetic excitation among the calcium antagonists. Levamlodipine may also be used to treat hypertension associated with heart failure, reverse ventricular hypertrophy, improve the relaxation function of the heart during the diastolic stage, protect the renal function with mild diuretic function, and prevent coronary heart disease, myocardial infarction, and stroke, and may further partially reverse abnormal circadian rhythm of blood pressure, and have mild anti-platelet effect, anti-myocardial ischemia effect, anti-arrhythmia effect, insulin sensitivity increasing effect and a certain anti-atherosclerosis effect. However, in a blood pressure depressing process, levamlodipine may easily cause sodium and water retention due to the high dosage, thus resulting in edema, so considerable patients withdraw, and the clinical application of levamlodipine is limited.

Indapamide is a non-thiazide diuretic antihypertensive medicine and a sulfonamide derivative, has a half-life of 17 h, and the metabolites thereof still have antihypertensive effect, so indapamide is a diuretic having a certain calcium antagonism. The antihypertensive mechanism of indapamide is complicated and includes that □ through the influence on the prostate substances, PGI2 (prostaglandin I2) and PGE2 (prostaglandin E2) are increased, and PCF2α (prostaglandin F2α) and TXA2 (thromboxane A2) are decreased, such that the hemorheology is improved, in which PGE2 and PGI2 have the function of dilating the coronary artery and peripheral vessels; □ through reduction of the response of the vascular wall to sodium ion, the calcium channels of the vascular wall cells are inhibited, and the sodium re-absorption of renal distal tubular is slightly inhibited, to relax the smooth muscle, dilate the vessels, and achieve the effects of diuresis and natriuresis, thus achieving the antihypertensive effects. The diuretic may mitigate the edema due to sodium and water retention caused by CCB, but indapamide has the side effect of glucose metabolism interference, so use of indapamide at high dose in long term may cause hypokalemia.

SUMMARY OF THE INVENTION

In view of the technical problems existing in depressing the blood pressure in the prior art of the edema side effect due to sodium and water retention caused when levamlodipine is administrated alone and the side effect of glucose metabolism interference caused when indapamide is administrated alone, the present invention is directed to an antihypertensive pharmaceutical composition.

The antihypertensive pharmaceutical composition of the present invention includes levamlodipine or a pharmaceutically acceptable salt thereof, and indapamide.

In the present invention, as levamlodipine and indapamide are administrated in combination, the dosages of levamlodipine and indapamide in the treatment process are reduced, and the same or even better antihypertensive effect is achieved. Moreover, as levamlodipine and indapamide are administrated at a low dose, the edema side effect due to sodium and water retention caused by levamlodipine and the side effect of glucose metabolism interference caused by indapamide are decreased. Furthermore, the edema side effect due to sodium and water retention caused by levamlodipine may be further decreased due to the diuretic property of indapamide.

In the present invention, a weight ratio of levamlodipine to indapamide is 1:0.04-1, and preferably 1:0.2-1.

The pharmaceutically acceptable salt is one or more selected from levamlodipine benzenesulfonate, levamlodipine mesylate, levamlodipine acetate, levamlodipine aspartate, levamlodipine tartrate, levamlodipine maleate, levamlodipine sulfate, levamlodipine hydrochloride, and levamlodipine hydrobromide.

The antihypertensive pharmaceutical composition of the present invention further includes a pharmaceutically acceptable adjuvant.

In the antihypertensive pharmaceutical composition of the present invention, a content of levamlodipine is preferably 0.1-30 wt %, more preferably 0.25-5 wt %; and a content of indapamide is preferably 0.01-5 wt %, and more preferably 0.05-2.5 wt %.

The pharmaceutically acceptable adjuvant is one or more selected from microcrystalline cellulose, pregelatinized starch, lactose, hydroxymethyl starch sodium, magnesium stearate, talc, and polyvinylpyrrolidone (referred to as PVP-k30).

The antihypertensive pharmaceutical composition of the present invention further includes a pharmaceutically acceptable diluent, adhesive, disintegrant, lubricant, coloring agent and/or flavoring agent.

The antihypertensive pharmaceutical composition of the present invention may be prepared into an oral preparation, such as, a tablet or a capsule, in which the tablet may be coated with a sugar coat or a film coat, or be not coated.

The present invention has the following effective and active effects. As levamlodipine and indapamide are administrated in combination, a good synergistic antihypertensive effect is achieved. The dosage of levamlodipine and indapamide is decreased, while the same or even better antihypertensive effect is achieved. Moreover, low dose of levamlodipine may also decrease the edema side effect due to sodium and water retention caused by levamlodipine, and the diuretic property of indapamide may further decrease the edema side effect due to sodium and water retention caused by levamlodipine. Furthermore, low dose of indapamide may also decrease the side effect of glucose metabolism interference caused by indapamide.

BRIEF DESCRIPTION OF THE DRAWINGS

No drawings

DETAILED DESCRIPTION OF THE INVENTION

Embodiments 1-2 Compound tablets

TABLE 1

Compositions and doses of compound tablets of Embodiments 1-2

| Compositions | Embodiment 1 | Embodiment 2 |
|---|---|---|
| Levamlodipine benzenesulfonate (g) | 2.5 (based on levamlodipine) | 0.2 (based on levamlodipine) |
| Indapamide (g) | 0.1 | 0.02 |
| Microcrystalline cellulose (g) | 30 | 40 |
| Pregelatinized starch (g) | 77.4 | 105.78 |
| Lactose (g) | 30 | 40 |
| Hydroxymethyl starch sodium (g) | 9 | 12 |
| Magnesium stearate (g) | 1 | 2 |
| 95% ethanol | suitable amount | suitable amount |
| In total (tablets) | 1000 | 1000 |

Preparation process: Levamlodipine benzenesulfonate, indapamide, microcrystalline cellulose, pregelatinized starch, lactose, and hydroxymethyl starch sodium were placed in a mortar, and uniformly mixed by grinding, screened with a 20-mesh sieve, added into a suitable amount of 95% ethanol to obtain a soft material, screened with a 20-mesh sieve, granulated, and air dried at 40° C. The dried granules were finished with a 16-mesh sieve, added with magnesium stearate, uniformly mixed and then tableted.

Embodiments 3-4 Compound capsules

TABLE 2

Compositions and doses of compound capsules of Embodiments 3-4

| Compositions | Embodiment 3 | Embodiment 4 |
|---|---|---|
| Levamlodipine benzenesulfonate (g) | 2.5 (based on levamlodipine) | 60 (based on levamlodipine) |
| Indapamide (g) | 2.5 | 10 |
| Microcrystalline cellulose (g) | 135 | 120 |
| Talc (g) | 4 | 5.4 |
| 0.5% solution of PVP-k30 in ethanol | suitable amount | suitable amount |
| In total (capsules) | 1000 | 1000 |

Preparation process: levamlodipine benzenesulfonate, indapamide, and microcrystalline cellulose were placed in a mortar, and uniformly mixed by grinding, screened with a 20-mesh sieve, added into a suitable amount of 0.5% solution of PVP-k30 in ethanol to obtain a soft material, screened with a 20-mesh sieve, granulated, and air dried at 40° C. The dried granules were finished with a 16-mesh sieve, added with talc, uniformly mixed, and then capsulated.

Effect Embodiment 1 Blood pressure depressing test in rats

Experiment method: 50 health spontaneous hypertension SHR rats (female to male 1:1, weight 200-240 g) were equally divided into 5 groups according to the level of the hypertension (the specific grouping method is as shown in Table 3), and intragastrically administrated with the medicine. For the blood pressure of the rate, the systolic pressure at the tail artery of the rat when being wake and quite was indirectly measured by an electronic blood pressure meter through the tail volume method respectively before administration and at the end of one, two, three, and four weeks after administration.

TABLE 3

Grouping of SHR rats

| Group | Number of rats | Administrated drug and dose |
|---|---|---|
| Blank model group | 10 | Equal volume of 0.9% saline |
| Levamlodipine group | 10 | 5 mg levamlodipine benzenesulfonate/kg$^-$ · d |
| Indapamide group | 10 | 5 mg indapamide/kg · d |
| Compound low-dose group | 10 | 2.5 mg levamlodipine benzenesulfonate/kg · d + 0.5 mg indapamide/kg · d |
| Compound high-dose group | 10 | 2.5 mg levamlodipine benzenesulfonate/kg · d + 2.5 mg indapamide/kg · d |

Note:
2.5 mg levamlodipine benzenesulfonate/kg · d in Table 1 is calculated based on levamlodipine Experimental results: the levamlodipine group, the indapamide group, the compound low-dose group, the compound high-dose group have significant antihypertensive effect, compared with the blank model group; the compound low-dose group, and the compound high-dose group have significant antihypertensive effect, compared with the levamlodipine group and the indapamide group. The specific experimental results are as shown in Table 4. In view of the edema side effect, no edema occurred in the blank model group, the indapamide group, the compound low-dose group, and the compound high-dose group, while edema occurred at an incidence rate of 10% in the levamlodipine group.

TABLE 4

Influence on blood pressure of SHR rats of administration of levamlodipine, indapamide, and compound preparations thereof

| Group | Before administration (KPa) | 1 week after administration (Kpa) | 2 weeks after administration (KPa) | 3 weeks after administration (KPa) | 4 weeks after administration (KPa) |
|---|---|---|---|---|---|
| Blank model group | 27.09 ± 1.24 | 27.23 ± 1.11 | 26.81 ± 1.25 | 26.96 ± 1.44 | 27.14 ± 1.34 |
| Levamlodipine group | 26.96 ± 1.29 | 26.79 ± 1.31 | 25.33 ± 1.26# | 24.55 ± 1.28# | 23.87 ± 1.28# |
| Indapamide group | 27.02 ± 1.39 | 26.88 ± 1.38 | 25.85 ± 1.38# | 25.56 ± 1.35# | 25.36 ± 1.36# |
| Compound low-dose group | 26.72 ± 1.78 | 26.55 ± 1.82 | 24.79 ± 1.69#■ | 23.73 ± 1.56#■ | 22.68 ± 1.53#●■ |
| Compound high-dose group | 26.79 ± 1.44 | 26.61 ± 1.45 | 24.78 ± 1.39#▲■ | 23.67 ± 1.32#▲■ | 22.51 ± 1.14#▲■ |

Note:
compared with the blank model group, $p < 0.01$,
●compared with the levamlodipine group, $p < 0.05$,
▲compared with the levamlodipine group, $p < 0.01$,
■compared with the indapamide group, $p < 0.01$.

Conclusions: the compound preparations of levamlodipine and indapamide have a better antihypertensive effect than levamlodipine and indapamide, and there is significantly difference in the anti-hypertensive effects. The combined administration of levamlodipine and indapamide has a certain synergistic effect on the spontaneous hypertension rats, and has a therapeutic effect superior to those of the two medicines administrated alone, and the combined administration does not induce the edema side effect due to sodium and water retention.

What is claimed is:

1. An antihypertensive pharmaceutical composition, comprising levamlodipine or a pharmaceutically acceptable salt thereof, and indapamide having a weight ratio of levamlodipine to indapamide of 1:0.04-1.

2. The antihypertensive pharmaceutical composition according to claim 1, wherein the weight ratio of levamlodipine and indapamide is 1:0.2-1.

3. The antihypertensive pharmaceutical composition according to claim 1, wherein the pharmaceutically acceptable salt is one or more selected from levamlodipine benzenesulfonate, levamlodipine mesylate, levamlodipine acetate, levamlodipine aspartate, levamlodipine tartrate, levamlodipine maleate, levamlodipine sulfate, levamlodipine hydrochloride, and levamlodipine hydrobromide.

4. The antihypertensive pharmaceutical composition according to claim 1, further comprising a pharmaceutically acceptable adjuvant.

5. The antihypertensive pharmaceutical composition according to claim 4, wherein a content of levamlodipine is 0.1-30 wt %, and a content of indapamide is 0.01-5 wt %.

6. The antihypertensive pharmaceutical composition according to claim 5, wherein the content of levamlodipine is 0.25-5 wt %, and the content of indapamide is 0.05-2.5 wt %.

7. The antihypertensive pharmaceutical composition according to claim 4, wherein the pharmaceutically acceptable adjuvant is one or more selected from microcrystalline cellulose, pregelatinized starch, lactose, hydroxymethyl starch sodium, magnesium stearate, talc, and polyvinylpyrrolidone.

8. The antihypertensive pharmaceutical composition according to claim 4, further comprising a pharmaceutically acceptable diluent, adhesive, disintegrant, lubricant, coloring agent and/or flavoring agent.

9. The antihypertensive pharmaceutical composition according to claim 4, wherein the pharmaceutical composition is a tablet or a capsule.

10. An antihypertensive pharmaceutical composition, consisting essentially of levamlodipine or a pharmaceutically acceptable salt thereof, and indapamide having a weight ratio of levamlodipine to indapamide of 1:0.04-1.

11. The antihypertensive pharmaceutical composition according to claim 10, wherein the weight ratio of levamlodipine and indapamide is 1:0.2-1.

12. The antihypertensive pharmaceutical composition according to claim 10, wherein the pharmaceutically acceptable salt is one or more selected from levamlodipine benzenesulfonate, levamlodipine mesylate, levamlodipine acetate, levamlodipine aspartate, levamlodipine tartrate, levamlodipine maleate, levamlodipine sulfate, levamlodipine hydrochloride, and levamlodipine hydrobromide.

13. The antihypertensive pharmaceutical composition according to claim 10, further comprising a pharmaceutically acceptable adjuvant.

14. The antihypertensive pharmaceutical composition according to claim 13, wherein the pharmaceutically acceptable adjuvant is one or more selected from microcrystalline cellulose, pregelatinized starch, lactose, hydroxymethyl starch sodium, magnesium stearate, talc, and polyvinylpyrrolidone.

15. The antihypertensive pharmaceutical composition according to claim 10, wherein a content of levamlodipine is 0.1-30 wt %, and a content of indapamide is 0.01-5 wt %.

16. The antihypertensive pharmaceutical composition according to claim 10, wherein the content of levamlodipine is 0.25-5 wt %, and the content of indapamide is 0.05-2.5 wt %.

17. The antihypertensive pharmaceutical composition according to claim 10, wherein the pharmaceutical composition is a tablet or a capsule.

18. An antihypertensive pharmaceutical composition, consisting of levamlodipine or a pharmaceutically acceptable salt thereof, and indapamide having a weight ratio of levamlodipine to indapamide of 1:0.04-1.

19. The antihypertensive pharmaceutical composition according to claim 18, wherein the weight ratio of levamlodipine and indapamide is 1:0.2-1.

* * * * *